United States Patent [19]

Stolarczyk

[11] E Patent Number: Re. 32,563

[45] Reissued Date of Patent: Dec. 15, 1987

[54] CONTINUOUS WAVE MEDIUM FREQUENCY SIGNAL TRANSMISSION SURVEY PROCEDURE FOR IMAGING STRUCTURE IN COAL SEAMS

[75] Inventor: Larry G. Stolarczyk, Raton, N. Mex.

[73] Assignee: Stolar, Inc., Raton, N. Mex.

[21] Appl. No.: 889,896

[22] Filed: Jul. 28, 1986

Related U.S. Patent Documents

Reissue of:

[64] Patent No.: 4,577,153
Issued: Mar. 18, 1986
Appl. No.: 731,741
Filed: May 6, 1985

U.S. Applications:

[63] Continuation-in-part of Ser. No. 483,264, Apr. 8, 1983, abandoned.

[51] Int. Cl.[4] ..... G01V 3/12; G01V 3/30

[52] U.S. Cl. ..... 324/334; 324/337; 324/338

[58] Field of Search ..... 324/334–338, 324/341; 166/248, 250

[56] References Cited

U.S. PATENT DOCUMENTS

| | | | |
|---|---|---|---|
| 3,440,523 | 4/1969 | Gabillard | 324/337 |
| 4,045,724 | 8/1977 | Shuck et al. | 324/338 |
| 4,161,687 | 7/1979 | Lytle et al. | 324/338 |
| 4,275,787 | 6/1981 | Helbig . | |

FOREIGN PATENT DOCUMENTS

| | | | |
|---|---|---|---|
| 0055330 | 4/1912 | Austria | 324/338 |
| 0105801 | 4/1984 | European Pat. Off. . | |
| 0143480 | 8/1980 | Fed. Rep. of Germany | 324/338 |
| 2535259 | 10/1977 | Fed. Rep. of Germany | 324/334 |
| 1018188 | 1/1966 | United Kingdom . | |
| 1057519 | 2/1967 | United Kingdom | 324/338 |

OTHER PUBLICATIONS

Grubb et al., "Borehole Measurements of . . . in the 300 kHz to 25 mHz Frequency Range", Radio Science, vol. 11, No. 4, pp. 275–283, Apr. 1976.

Lytle et al., "Using Electromagnetic Remote Probing to Determine . . . Properties of a Coal Seam", Geophysics, vol. 41, No. 2, Apr. 1976, pp. 363, 364.

Cook, John C., Borehole-Radar Exploration in a Coal Seam, Geophysics, vol. 42, No. 6, Oct. 1977, pp. 1254–1257.

Lytle et al., "Cross-Borehole Electromagnetic Probing to Locate . . . Anomalies", Geophysics, vol. 44, No. 10, (Oct. 1979), pp. 1667–1676.

"The Design of a Cellular MF Radio Communication System for Underground Mining", Larry G. Stolarczyk, IEEE Conference, 11/30–12/14, 1980.

"Systems Design and Performance of an MF Radio Communication System for Underground Mining", Larry G. Stolarczyk, Robert L. Chuto, IEEE Conference, 5/9–5/10, 1981.

"Performance of a Minewide Wireless Underground Medium Frequency Communication System", Larry G. Stolarczyk, Robert Chufo, (1981).

A Whole Mine Medium Frequency Radio Communication System, Harry Dobroski, Jr.; Larry G. Stolarczyk.

*Primary Examiner*—Gerard R. Strecker
*Attorney, Agent, or Firm*—Thomas E. Schatzel

[57] ABSTRACT

Instrumentation and procedures for detecting geological anomalies occurring in layered coal formations. The instrumentation comprises a medium frequency continuous wave narrowband FM transmitter and receiver pair. Two instrument configurations are disclosed with one being a portable instrument for use with an existing mined area and another being a downhole instrument for insertion into boreholes in unmined areas. Survey procedures are provided to detect anomolies through signal attenuation, path attenuation and signal phase shift. Continuity measurements provide data to determine the existance of anomalies. Tomographic techniques are employed to provide a visual image of the anomaly. Computer aided reconstruction techniques provide such visual images from the generated data.

20 Claims, 12 Drawing Figures

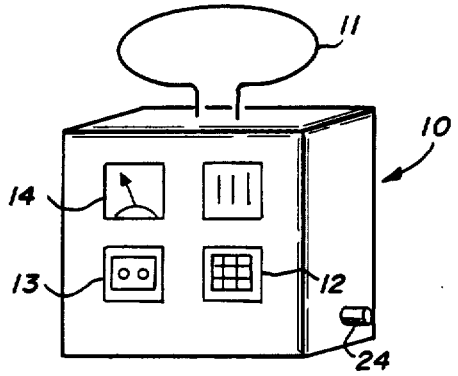
Fig_1
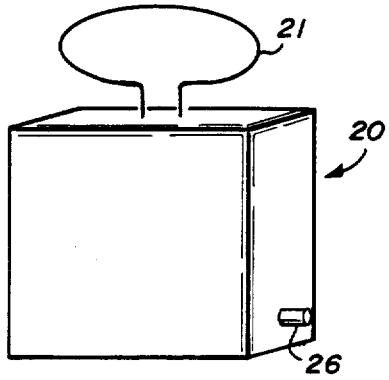
Fig_2
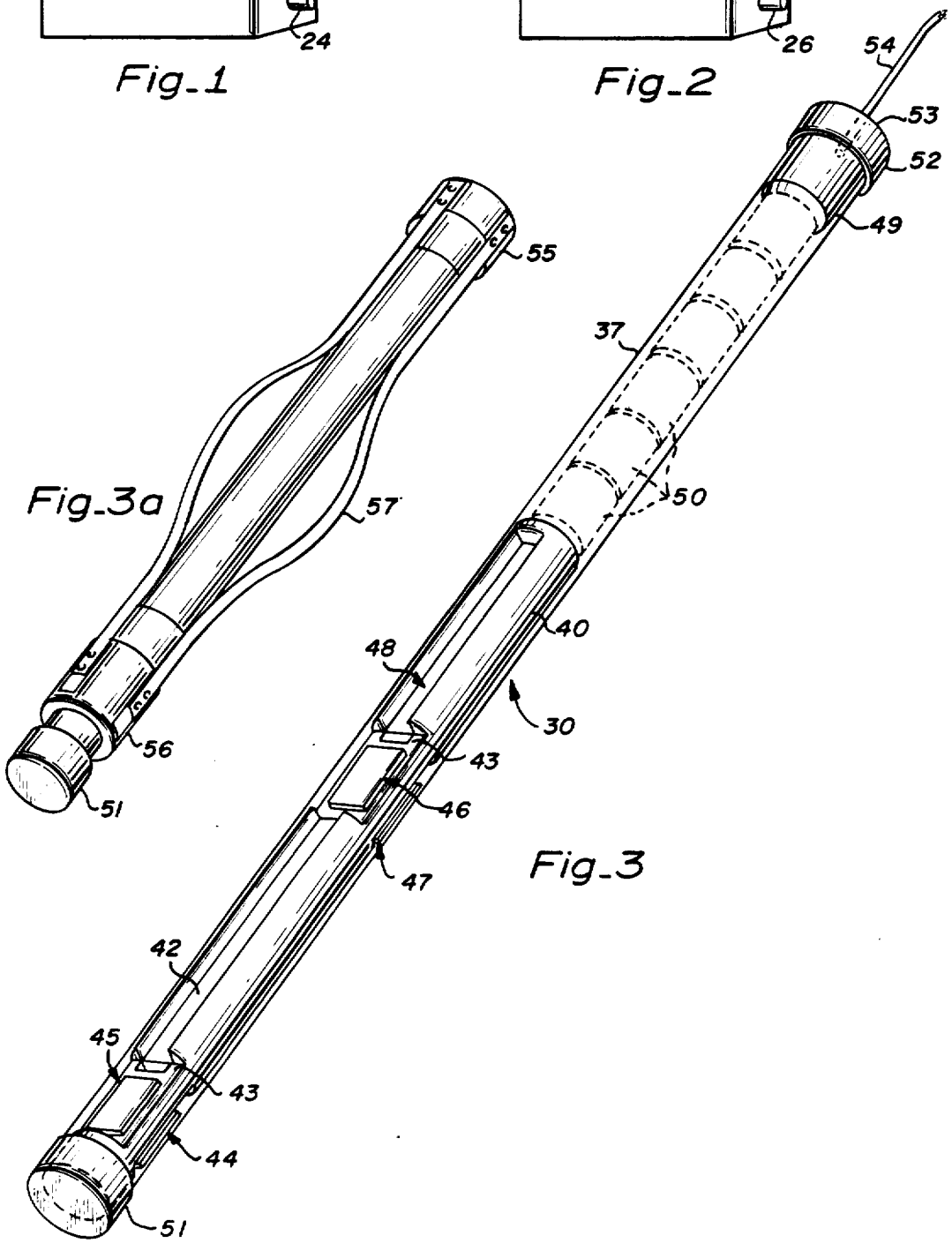
Fig_3a
Fig_3

CONTINUOUS WAVE MEDIUM FREQUENCY SIGNAL TRANSMISSION SURVEY PROCEDURE FOR IMAGING STRUCTURE IN COAL SEAMS

Matter enclosed in heavy brackets [ ] appears in the original patent but forms no part of this reissue specification; matter printed in italics indicates the additions made by reissue.

This is a continuation-in-part of co-pending application Ser. No. 483,264 filed on Apr. 8, 1983, now abandoned.

BACKGROUND OF THE INVENTION

1. Field of the Invention

This invention relates generally to instrumentation and procedures for detecting geological anomalies in coal seams and more specifically to continuous-wave medium frequency radio imaging techniques combined with computer aided reconstruction to provide graphic radiogenic images of seam anomalies.

2. Description of the Prior Art

Coal seams or deposits occurring in layered formations have been distorted by many different types of geological mechanisms. Differential compaction occurring in surrounding layers causes faults, twists and rolls to occur in the seam. Ancient streams have washed coal from beds leaving sand and rock deposits. These deposits, known as fluvial channel sand scours, can cause washouts and weak roof. Such seam distortions and rock deposits are physical barriers to mining equipment. Two types of underground mining techniques are extensively used in the coal mining industry. One type, referred to as room and pillar, or continuous mining can mine around many of these barriers. The continuous mining technique is less expensive and requires less manpower. For example, set-up generally requires three shifts of eight people. Continuous mining, however, produces only approximately 300 tons per shift. Longwall mining, the other widely used technique, is much more efficient in uniform coal beds. This method yields production rates averaging 1500 tons per shift.

In the United States, the Mining Safety and Health Administration requires that retreating, rather than advancing longwalls be used. On the other hand, in Europe, advancing longwalls are extensively used. Retreating longwalls are set up to mine in the direction of the main entry, whereas advancing longwalls mine away from the main entry. Continuous mining techniques are employed to set up the retreating longwall. From the main entry, two entry ways are mined at right angles to the main entry and on either side of the longwall panel. These entry ways, the head-gate entry and tail-gate entry respectively, extend the length of the longwall panel. At the end of the panel, a crosscut is made between the head gate and tail gate entries. The wall of the crosscut facing the main entry is the longwall face. The longwall machine is set up along the face with a heading towards the main entry. As the longwall moves forward, the roof caves in over the mined out area. A barrier block of unmined coal is left at the end of the run to support the roof over the main entry.

The high yield of longwall mining makes it economically advantageous to use where a long panel can be mined. A typical longwall panel contains from 500,000 to one million tons of coal. The initial investment and set-up cost of longwall mining are high. Equipment cost averages many millions of dollars. Longwall set-up requires thirty days minimum, at three shifts per day with twelve to fourteen men per shift. Thus, set-up expenses are very large as a result and to achieve the low cost production advantage of the longwall method a uniform coal seam is necessary to ensure a long production run. Seam anomalies such as faults, washouts, interbeddings and dikes can cause premature termination of the longwall production run. In many instances, longwalls become "ironbound" after encountering an anomaly. Removal of such "ironbound" equipment requires blasting which can damage equipment and exposes miners to extreme danger. Accordingly, if seam anomalies could be detected and analyzed in advance of mining, the mining techniques could be planned for minimum production cost. Where the survey discloses a long continuous coal seam, the low cost longwall technique can be employed. If barriers to longwall mining are discovered the mine engineering department can use continuous mining to mine around the barriers, or the anomalies can be removed, for example by fracking or blasting.

Geological surveys for potentially productive coal formations use many well known procedures. These procedures employ a wide variety of technologies. Satellite imaging and photography provide global data for use by mine geologists. However, because of the broad overview of the data are of no value in determining the mineability of a coal seam. Macrosurvey (foot prospecting) of surface strata and outcrop features enable geologists to forecast formation characteristics based upon prior knowledge. Surface based seismic and electromagnetic wave propagation procedures are extensively used in geophysical surveys for valuable deposits including oil and gas. These microsurvey techniques, however, are not reliable in examining the detailed structure of a coal seam.

Various microsurveying in-seam seismic techniques are currently employed to yield useful data concerning seam anomalies. A technique under development in Europe comprises firing shots from sixteen points into a block of 120 geophone groups, each consisting of thirty-six geophones. Computerized processing of the seismic data results in the detection of faults. To date, the procedure requires placing charges at five foot intervals and requires the installation of extensive cabling. Seismic techniques are primarily intended for advancing, rather than retreating longwalls. Further, this method has not proven to have the capability of resolving channel sand anomalies, especially for partial washouts and smaller, less significant anomalies, nor can they detect roof/-floor rock conditions. The emerging of the surface based spectral magnetotelluric method with controlled sources may have the capability of seeing into the earth's crust. This method appears to be useful in detecting major faults in layered formations, but cannot resolve detailed seam structure.

Downhole drilling has been used to probe longwall blocks. A ten-twelve hole pattern drilled six-hundred feet into the panel provides samples of the coal in the seam. This method, however, has the disadvantage of covering only a small percentage of the block. Because of this limited coverage this technique is not useful to detect and resolve seam anomalies that may exist in the seam between the boreholes. Surface core drilling and logging remains the most reliable source of seam information. Core sampling provides useful data in mapping stratified medium. Logging enables probing of the formation in the vicinity of the drill hole. None of the currently used logging methods can detect and resolve seam anomalies that may exist in the seam between the bore-holes over distances greater than about fifty feet. In-seam horizontal drilling can detect seam anomalies, but is subject to the same coverage limitations of vertical drilling. Horizontal drilling, additionally, is very expensive, averaging twenty cents per ton of coal produced.

Electromagnetic technologies have been investigated in an attempt to provide a geophysical method to see within the coal seams. Conventional and synthetic radar techniques have been reported in the literature. Because of the high frequency of the radar, it is exceedingly useful in investigating the geological structure in near proximity to the borehole. Deep seam penetration, however, requires very high transmit power in order to maintain any sort of useful resolution. This is because high frequency signals are attenuated very rapidly with distance in the seam. Accordingly, present radar methods cannot see deep into the seam.

Publications by R. J. Lytle, Cross Borehole Electromagnetic Probing to Locate High-Contrast Anomalies, Geophysics, Vol. 44, No. 10, Oct. 1979; and Computerized Geophysical Tomography, Proceedings of the IEEE, Vol. 67, No. 7, July 1979, have described a method of imaging coal seams using continuous wave (CW) signals. His method proposed only tomographic imaging between nearby boreholes. The method of Lytle had limited range and resolution, because of the limited spatial measurements that could be taken using downhole probes. To satisfy the requirements for tomography, Lytle used a higher frequency range, thus achieving less range. Further, the conductivity of rock was found to be much greater than the conductivity of coal. Where the difference conductivity (contrast) is large, the tomography algorithm will diverge rather than converge, resulting in no image.

A study conducted by Arthur D. Little, Inc. for the U.S. Bureau of Mines investigated continuous-wave medium-frequency signal propagation in coal. The results, published by Alfred G. Emslie and Robert L. Lagace, Radio Science, Vol. II, No. 4, April 1976, dealt with the use of electromagnetic waves for communication purposes only. Additionally, errors may be present in the wave propagation equations employed. United Kingdom Pat. No. 1,018,188, issued to Kaiser, discloses a method for testing various media utilizing high frequency radio waves. A well logging method and apparatus is disclosed in EPO Patent Application No. 0 105801, assigned to Schlumberger Limited. The method is not directed to deep seam penetration and imaging, but is used to obtain conductivity and dielectric measurements proximate to a borehole.

Other electromagnetic techniques suffer similar range and resolution problems. None of the prior art recognized the existance of a coal seam transmission window in the 300–800 kHz range. Accordingly, none of the prior art achieved a long range, high resolution imaging of geological anomalies.

BRIEF DESCRIPTION OF THE INVENTION

Accordingly, it is an object of the present invention to provide instrumentation and procedures for in-seam and surface imaging of coal seam anomalies with a range sufficient to image an entire longwall panel.

It is a further object of the present invention to provide instrumentation and procedures to image coal seam anomalies with resolution sufficient to detect faults, full and partial washouts, fluvial channel sand scours, dikes and interbeddings.

It is a further object of the present invention to minimize production costs by surface mappng of fault directions, and providing longwall headings where appropriate.

It is another object of the present invention to minimize production costs by in-seam imaging of longwall panels, after the panel headings have been developed.

An additional object of the present invention is to mitigate or eliminate hazards to miners resulting from unexpected geological anomalies.

It is another object of the present invention to measure coal seam heights.

It is a further object of the present invention to provide detailed in-seam imaging of the seam in advance of the longwall.

It is a further object of the present invention to predict roof falls.

It is a further object of the present invention to verify predicted anomalies by signal strength measuring means.

Briefly, a preferred embodiment of the present invention includes a continuous-wave medium frequency transmitter with FM capabilities and equipped with a directional loop antenna, a continuous wave medium frequency receiver equipped with a directional loop antenna and capable of accurately measuring and recording the received signal amplitude and phase shift of the transmitted signal, and data processing means for producing a pictorial representation of the coal seam from the raw data generated. Both the transmitter and the receiver are portable and are designed in two configurations: a cylindrical configuration, referred to as a sonde, for insertion down boreholes in a coal seam, and a portable, or entry configuration adaptable for in-seam use.

The invention further includes survey procedures for imaging structures in coal seams. Two methods of seam imaging are provided with procedure selection dependent on terrain and seam depth. Surface based seam imaging with downhole continuity instruments is expected to be used in moderately shallow beds with good surface drilling conditions. In-seam imaging with tomographic techniques will be used when a clear picture of the seam structure is required. Combination techniques, utilizing both downhole and in-seam measurements may be used for improved resolution as circumstances dictate.

The preferred embodiment utilizes continuous wave medium frequency (MF) signals to achieve high resolution imaging of geophysical anomalies in coal seams with relatively low output power. The medium frequency range is generally defined as being between approximately 300 KHz and approximately 3 MHz. Because the coal seam is bounded above and below by rock with a differing conductivity, at certain signal frequencies electromagnetic energy becomes trapped and will propagate over great distances. This transmission window, or coal seam mode is excited by the tuned loop antennas employed in the preferred embodiment causing the MF signals to travel several hundred meters in the coal seam. Seam anomalies create regions with different electrical constitutive parameters relative to the coal. This electrical contrast between the coal and the anomalous structure gives rise to the imaging method. The contrast will change the wave propagation constant in the region whereby the wave received on the far side of the region can be analyzed to determine structure between the transmitter and receiver.

The MF in-seam continuity and tomography instruments further employ FM signals with a narrow occupied spectrum bandwidth. The receiving instruments detect and measure the signals with phase-locked-loop (PLL) techniques. PLL receivers extend the signal detection threshold well into the noise, thus enhancing operating range. The continuity imaging procedure is used where relatively large electrical contrast between the coal seam and anomalous structure is present. Tomography is applicable when a small electrical contrast exists. Tomography instrumentation can improve resolution by making more spatial measurements, thus overcoming the inherent radar range limitations.

The downhole procedure will require a drilling plan that will enable the medium frequency signals to propagate in the seam between boreholes. In this procedure, a plurality of holes are drilled on either side of the seam. The transmitter and receiver probes are inserted into the boreholes on opposite sides of the seam and signal attenuation is measured across the seam. A series of data points is generated by varying the location of the transmitter and receiver across the series of boreholes. Signal attenuation, path attenuation, and phase shift are measured and compared with calculated values to determine if seam anomalies are present. Additionally these data can be reconstructed by computer assisted imaging techniques to provide a pictorial representation of the seam. When a fault is detected additional boreholes are drilled bisecting boreholes in the original drilling plan and further readings are taken to localize the fault. The in-seam imaging technique is carried out in a similar manner to the surface based imaging technique except the transmitter and receiver instruments are located in the head and tail gate entries adjacent to the seam.

Additionally, the instrumentation can be used to improve mining safety by detecting coal seam fire headings. Fire in the seam affects the coal seam's conductivity and will thus be detected in the same manner as anomalies are detected. Where a fire is known to exist the in-seam detection methods are used to localize it so it can be controlled. In another application, communications with trapped miners can be established by equipping the miners with small receivers or transceivers. By drilling in the suspected area of the trapped miner, the downhole instrument can excite the coal seam mode and be used to communicate with the trapped miner.

It is an advantage of the present invention that graphical representation of coal seam anomalies are developed by the imaging technique.

It is another advantage of the present invention that production costs can be minimized by selecting the appropriate mode of mining the coal.

It is a further advantage of the present invention that the imaging can be carried out using a minimum of equipment and a minimum of boreholes.

It is a further advantage of the present invention that imaging can be accomplished using a relatively low transmitter power.

It is a further advantage of the present invention that mining safety can be improved through the detection of geological anomalies in the working phase.

It is yet another advantage that partial washouts caused by fluvial channel sand scour can be detected by the present invention.

It is a further advantage that roof/floor rock conditions can be determined by the present invention.

It is yet another advantage of the present invention that the instrumentation can be used to communicate with trapped miners, thus increasing mining safety.

It is a further advantage that coal seam fire headings can be determined with the present invention.

It is a further advantage of the present invention that coal seam heights may be measured.

It is a further advantage of the present invention that detailed seam images can be obtained in advance of the longwall.

It is yet another advantage of the present invention that roof falls can be predicted.

It is a further advantage of the present invention that in-seam verification of anomalies can be performed.

These and other objects and advantages of the present invention will no doubt become obvious to those of ordinary skill in the art after having read the following detailed description of the preferred embodiments as illustrated in the various drawing figures.

IN THE DRAWINGS

FIG. 1 is a front elevational view of an in-seam receiver for use in the present invention;

FIG. 2 is a front elevational view of an in-seam transmitter for use in the present invention;

FIG. 3 is a cut away view of a downhole probe for use in the present invention;

FIG. 3a is a front elevational view of a downhole probe fitted with a borehole probe centralizer;

DESCRIPTION OF THE PREFERRED EMBODIMENT

Figure 4:
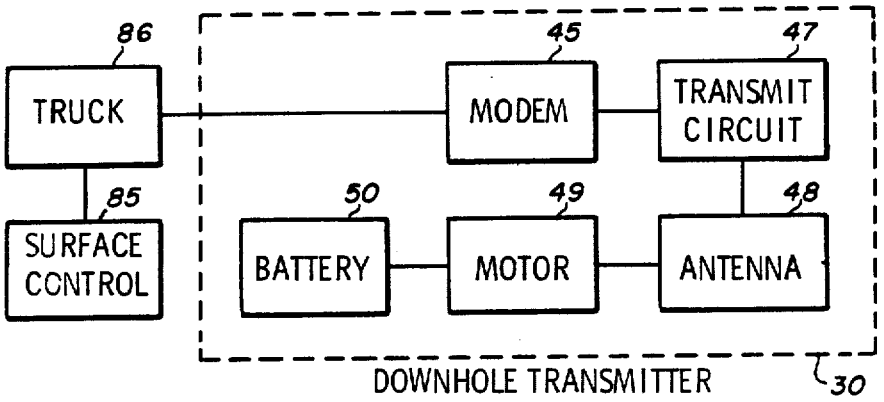
FIG. 4 is a schematic representation of the modular components of the downhole receiver and transmitter probes of FIG. 3.
Figure 4:
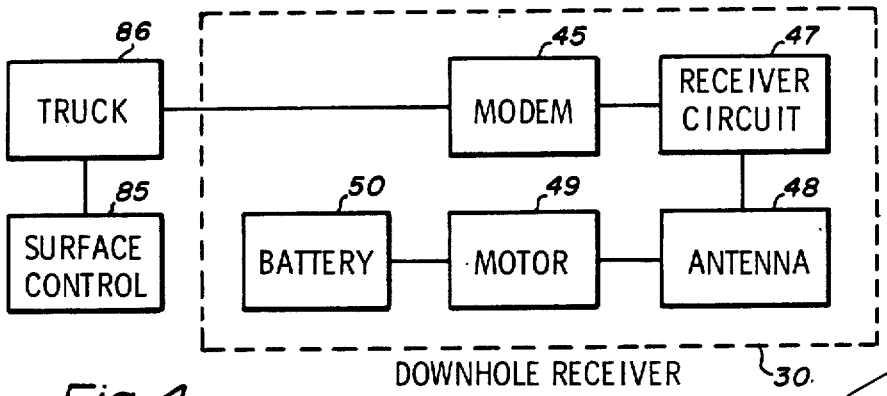

FIG. 1 illustrates a portable continuous-wave medium-frequency (CW MF) receiver for in-seam tomographic imaging. As used herein, tomography is a generic term to denote an electromagnetic process of imaging structure in a coal seam using medium frequency (MF) signals. The imaging process may or may not use the tomography algorithm. The receiver is designated by the general reference character 10 and is of the single conversion, superheterodyne type with a frequency range of 300 to 800 kHz, tunable in five kHz increments. Receiver 10 is designed to automatically measure field strength of a transmitted signals, and to convert this measured field strength into a digital signal for subsequent data processing. Receiver 10 includes a tuned looped antenna 11, a distance logging keyboard 12, a magnetic tape recorder 13 and a field strength display 14.

Figure 5:
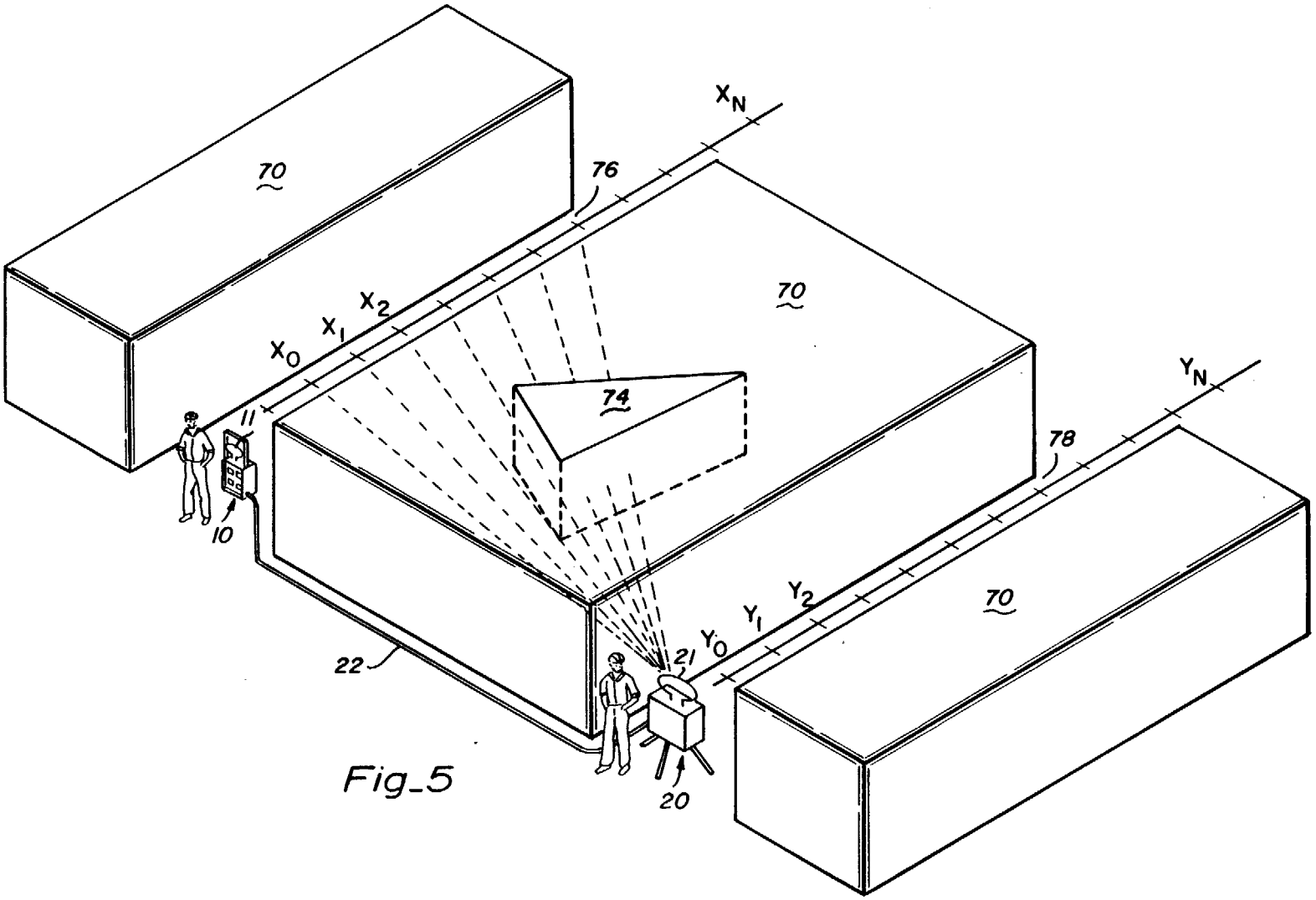
FIG. 5 is a idealized cut away view of a coal seam, showing the location of transmitter of FIG. 2 and receiver of FIG. 1 for in-seam tomography.

FIG. 2 illustrates a continuous-wave medium-frequency transmitter referred to by the general reference character 20. The transmitter 20 is a class B transmitter with a frequency range of 300 to 800 kHz, tunable in five kHz increments. The output power of transmitter 20 is twenty watts. This is sufficient to provide a range of at least 1550 feet at 520 kHz, depending on the medium. Transmitter 20 is equipped with a tuned loop antenna 21. The transmitter antenna 21 and the receiver antenna 11 may be constructed, for example, by sandwiching a predetermined number of turns of wire between a pair of flexible elastic strips of plastic material, and securing the strips in a circle. The plastic strips can temporarily deform to allow passage through tight quarters, and may be formed of a flexible plastic sold under the trademark "Lexan". The transmitter 20 and receiver 10 are constructed in a configuration adaptable for in-seam use as later described herein and illustrated in FIG. 4. In addition to the continuous wave signal capability of receiver 10 and transmitter 20, the transmitter 20 is further designed to generate and transmit narrowband frequency modulation (FM) signals, and the receiver 10 is further designed to receive narrowband FM signals and to demodulate those signals. This capability allows for phase shift measurements which yields additional useful data in detecting and imaging the geological anomalies. For such measurements, a reference signal must be sent from the transmitter 20 to the receiver 10. This signal is sent through fiber optics cable 22 as shown in FIG. 5. Fiber optics cable 22 is coupled to receiver 10 through reference cable connector 24, and is coupled to transmitter 20 through connector 26.

In-seam imaging requires access immediately adjacent to the coal seam. In situations where the head and tail gate entries have not been cut, as in the case of advancing longwall mining, or where the bed is moderately shallow with good surface drilling characteristics, surface based imaging employing downhole probes can be used. FIG. 3 illustrates the general configuration of a downhole probe, or sonde and referred to by the general reference character 30. The probe 30 is of a cylindrical configuration for insertion down a standard size borehole. Probe 30 includes an outer hollow structural cylinder 37 of a diameter of about two and one quarter inches. Cylinder 37 may be constructed of a variety of materials, and in the preferred embodiment is of a radiolucent material such as fiberglass. Rotatably mounted within cylinder 37 is a support frame 40. Support frame 40 is a solid cylinder with a longitudinal trough 42 ending at a pair of opposing flat faces 43. Mounted on each of the flat faces 43 is a modular circuit board including antenna heading control 44, modem 45 and either a receiver 46 or a transmitter 47 depending on whether receive or transmit capability is desired of the probe. Located in longitudinal trough 42 are conductors of a tuned loop antenna 48. Because of the directional nature of the radio transmissions through tuned loop antenna 48, means must be provided to mechanically orient the respective antennas of the receiver and transmitter probes to a co-planar alignment. This is accomplished by rotating the frame 40 within the outer cylinder 37 by means of a drive motor 49. Drive motor 49 is fixed to the proximal end of cylinder 37 and mechanically coupled to frame 40 whereby frame 40 can be rotated through a full 360° within cylinder 37. In the preferred embodiment, power to drive motor 49 is supplied by six nickel-cadmium batteries 50 fixed to the proximal end of support frame 40, just below drive motor 49. Cylinder 37 is sealed at its distal end by an end cap 51 and at its proximal end by an end cap 52. End cap 52 contains a standard four pin socket 53 into which is plugged into a cable 54. Cable 54 is the means by which the probe 30 is connected to surface equipment and through which data is sent for the imaging process. Electronic surface equipment for downhole receiver 30 comprises a signal strength display/recorder, a modem, and a radio transmitter/receiver for sending a reference signal between probes when the probes are operating in the FM mode.

To ensure that the probe is centrally located within the borehole, a borehole probe centralizer is fitted to the probe as shown in FIG. 3a. This centralizer includes a proximal end cap 55 which is attached to the probe proximal end cap 52. End cap 55 has a central aperture through which cable 54 may pass. Sleeve 56 fits snugly around the distal end of outer cylinder 40 of probe 30. Attached to both end cap 55 and sleeve 56 are three to four bands 57. These bands 57 are of a strong flexible material such as thin stainless steel. The bands 57 are prestressed to curve convexly outward to contact the inside walls of the borehole. The bands 57 are sufficiently flexible to urge the probe 30 into the borehole's center, and to allow for easy passage of the probe down the borehole. Downhole equipment and surface survey procedures can also be used within the mine, for example, as when unmined seams occur at lower levels than the seam being mined. In this situation, boreholes are drilled from the existing seam to the lower seam and downhole instruments and procedures are employed.

The preferred embodiment contemplates modular design of the components of both the downhole probes 30 and the in-seam instruments 10 and 20. In this way cost of production is reduced and repair and servicing is simplified. FIG. 4 is a general block diagram of the components, showing the modular design.

Table 1 is an equipment identification chart identifying the modular components and Table 2 is a configuration matrix showing the composition of each downhole probe 30 and in-seam instrument 10 and 20.

TABLE 1

| Module | Identification |
|---|---|
| A1 | Receiver |
| A3 | Transmitter |
| A10 | $C^3$ Modem |
| A13 | Display/Recorder |
| B6 | NiCad Battery |
| | Tuned Loop Antenna |
| | Enclosures |
| C1 | Downhole |
| C2 | Portable |

TABLE 2

CONFIGURATION MATRIX

| Instrument | A1 | A3 | A10 | A13 | B6 | C1 | C2 |
|---|---|---|---|---|---|---|---|
| Downhole 30 | | | | | | | |
| Transmitter | | 1 | 1 | | 1 | 1 | |
| Receiver | 1 | | 1 | | 1 | 1 | |
| Surface | | | 1 | 1 | | | |
| In-seam (10 or 20) | | | | | | | |
| Transmitter 20 | | 1 | | | 1 | | 1 |

TABLE 2-continued

| CONFIGURATION MATRIX | | | | | | | |
|---|---|---|---|---|---|---|---|
| Instrument | A1 | A3 | A10 | A13 | B6 | C1 | C2 |
| Receiver 10 | 1 | | | 1 | 1 | | 1 |

Examples of equipment specifications are shown in the following Tables 3–7. Table 3 describes the general system operating parameters. Tables 4 and 5 illustrate the transmitter and receiver specifications, respectively. Table 6 describes the transmitter and receiver antenna characteristics and Table 7 gives the specifications for the modem.

TABLE 3

| SYSTEM SPECIFICATIONS | |
|---|---|
| Signal Emmissions: | |
| Type | CW and Narrowband FM |
| Frequency Range | 300 to 800 kHz |
| Tuning | 5 kHz Increments |
| Peak Deviation | 100 Hz |
| Modulation: | |
| Frequency Range | 200 Hz |
| Environmental: | |
| Operating Temperature | −40 to 80 Degree C. |
| Probe | 500 PSI |

TABLE 4

| Type | Complimentary Class B |
|---|---|
| Module Description | A3 |
| Frequency Range | 300 to 800 kHz |
| Tuning | 5 kHz Increments |
| Output Power | 20 Watts |
| Flatness | ± ½ dB |
| RF Load Impedance | 50 and 200 Ohms |
| VSWR | 3:1 Max |
| Mixer Oscillator | 10.7 MHz |
| Signal Oscillator | 100 Hz |
| Power Requirements | |
| Operating Voltage | 9 to 15 Volts DC |
| Demand Current | 3.5 Amperes |
| Connectors | |
| Type | Molex |
| Output Power | 2 |
| VCC | 1 |
| Ground | 1 |
| Fiber Optics Cable (Reference) | 1 |

TABLE 5

| RECEIVER | |
|---|---|
| Type | Single Conversion superheterodvne |
| Module Description | A1 |
| Frequency Range | 300 to 800 kHz |
| Tuning | 5 kHz Increments |
| IF Frequency | 10.7 MHz |
| Source Impedence | 50 Ohms |
| Sensitivity | 0.1 Microvolts for 12 dB Sinad |
| IF Frequency | 10.7 MHz |
| Selectivity | |
| 3 dB BW | 200 Hz Mm |
| 70 dB BW | 1 kHz |
| Audio | |
| Squelched | 50 dB Mm |
| Unsquelched | 30 dB (100 UV) |
| Load | 8 Ohms |
| Frequency Response | |
| 3 dB | 10, 70, 100 Hz |
| Voltmeter | |
| Type | Synchronized with transmitter local oscillator |

TABLE 5-continued

| RECEIVER | |
|---|---|
| Type | Single Conversion superheterodvne |
| Range | 0 to 360 degrees |

TABLE 6

| ANTENNA | |
|---|---|
| Type | tuned Loop Antenna |
| Frequency Range | 300 to 800 kHz |
| Number of Turns | 11 |
| Magnetic Moment | |
| Downhole | 8 $ATM^2$ @ 20 W |
| Portable | 8 $ATM^2$ @ 20 W |
| Heading | |
| Type | Flux Gate Compass (Downhole) |

TABLE 7

Figure 6:
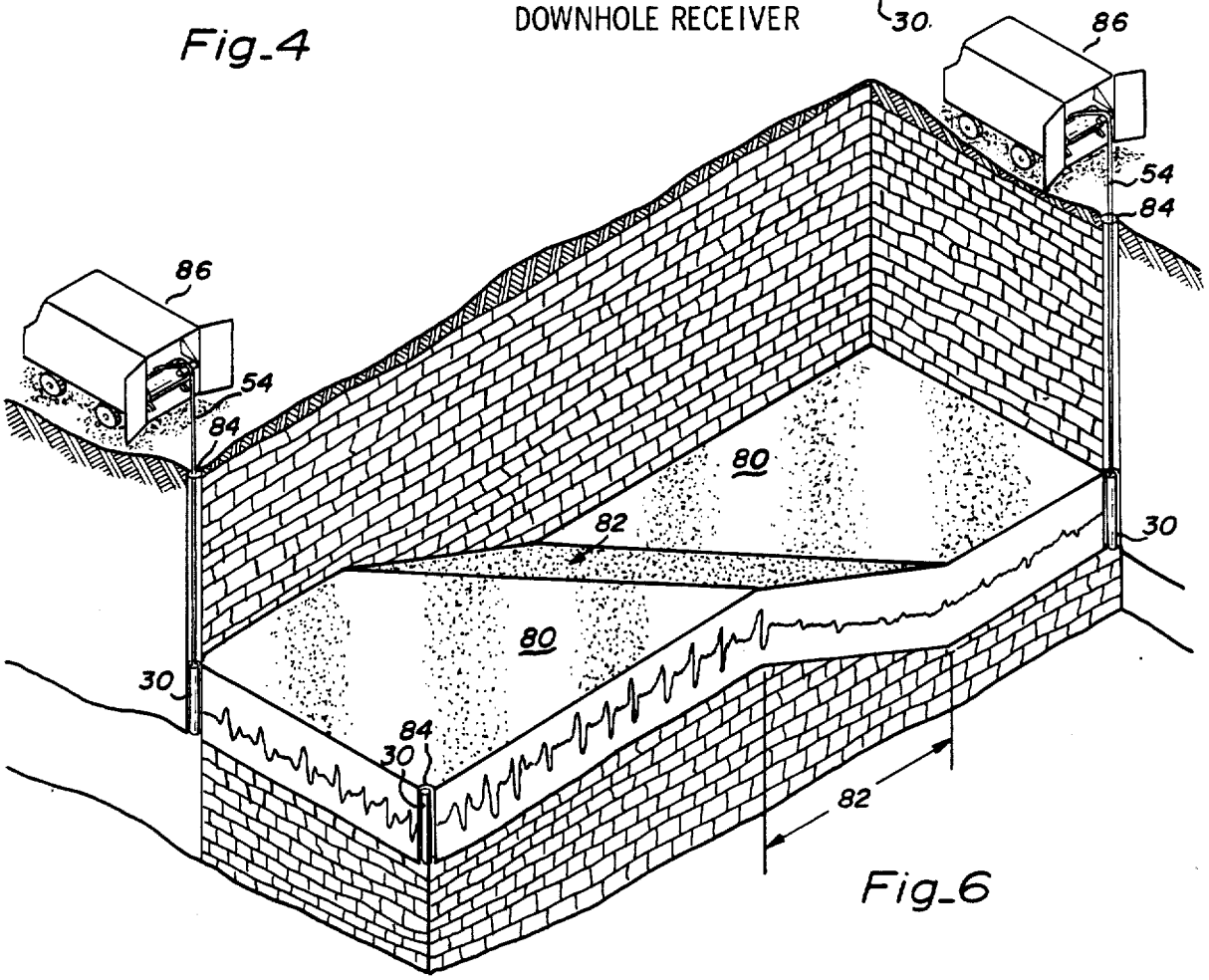
FIG. 6 is an idealized cut away view of a coal seam showing boreholes adjacent to the coal seam with downhole probes and surface equipment in position.

| $C^3$ MODEM | |
|---|---|
| Type | Manchester Code Format 1b Bit Code |
| Function | |
| Power | On/Off |
| Antenna Position | ± 30 of Command |

Where there is no immediate access to the coal seam, surface imaging is performed using the downhole probes 30 inserted into a series of boreholes around the seam's perimeter. This procedure is represented in FIG. 6.

Imaging of the seam is based upon the differential conductivity of coal and the anomalous structure. The conductivity of rock is several orders of magnitude greater than the conductivity of coal. The vertical orientation of the transmitting tuned loop antenna produces a horizontal magnetic field $H_\phi$ and a vertical electrical field $E_Z$. These fields are almost constant over the height of the coal seam. At large radial distances from the antenna, the fields decay exponentially at a rate determined by an effective attenuation constant ($\alpha$) which depends on losses both in the coal and in the rock, and on the dielectric constant of the coal. The attenuation rate is expected to increase as the coal seam thickness decreases, coal seam conductivity increases, and the relative dielectric constant increases. The attenuation rate decreases as the rock conductivity increases. The ratio also depends upon frequency of the transmitted signals, and on water content of the seam. Measured results by Enslie and Lagace indicate an attenuation rate in coal of approximately four dB/100 feet. This forms the basis for the coal seam continuity imaging method.

The tuned loop antennas excite the natural low loss coal seam mode signal in accordance with the following equation (1):

$$H_\phi = Mf(rah\epsilon_c\epsilon_r\sigma_c\sigma_r) \quad (1)$$

where M is the magnetic moment of the transmit antenna, r is the range from the transmitter to the receiver antennas, $\alpha$ is an attenuation constant, h equals the seam height, $\epsilon_c$ and $\epsilon_r$ are the seam and rock permitivities respectively, and $\sigma_c$ and $\sigma_r$ are the seam and rock conductivities.

The magnetic moment M is itself dependant on transmit power $P_o$, and bandwidth BW are represented by equation (2):

$$M = C\sqrt{\frac{P_o}{BW}} \quad (2)$$

Together, these equations indicate that the tuned loop antennas will excite the natural coal seam mode magnetic moment and thus provide the highest magnetic moment resulting in the longest range. Narrow system bandwidth also leads to improved receiver sensitivity and operating range. The receiver sensitivity [$S_{dB}^{10}$]

$$S_{dB}^{10}$$

for a 10 dB IF signal-to-noise ratio is given by equation (3):

$$[S_{dB}^{10} = -164 + 10\ \mathrm{Log}_{10}{}^{BW}\mathrm{IF} = 10\ \mathrm{Log}_{10}\mathrm{NF} \quad (3)]$$

$$[S_{dB}^{10} = -164 + 10\ \mathrm{Log}_{10}{}^{BW}\mathrm{IF} = 10\ \mathrm{Log}_{10}\mathrm{NF} \quad (3)]$$

$$S_{dB}^{10} = -164 + 10\ Log_{10}BW_{IF} + 10\ Log_{10}NF \quad (3)$$

where $BW_{IF}$ is the IF bandwidth of the signals and NF is the noise figure at the receiver.

Equation (3) thus shows that sensitivity increases as bandwidth decreases. The results of equations (1), (2) and (3) indicate that continuous wave MF signals are optimum for the geophysical survey instruments. This is because their narrow bandwidth results in signal propagation in coal with the lowest attenuation rate (Equation 3) and highest magnetic moment (Equations 1 and 2). The net result is that the operating range of the instruments is maximized at a specified output power.

The imaging method is dependent on a comparison of the calculated signal strength with the measured signal strength as determined by the CW, MF instruments. An analysis of the calculated signal strength is helpful to an understanding of the method. To provide a baseline reading for the imaging method, Equation (1), previously referred to, is used to calculate the expected signal strength in a particular coal seam. This is accomplished by measuring the various parameters at the particular seam and applying these results to Equation (1).

The propagated signal is received in the far side receiver. Because of either an increase in the "effective" seam conductivity or a decrease in height of the seam, wave propagation along a faulted seam path will result in greater attenuation rate. Thus, by comparing the level of a number of received signals, path anomalies can be detected. Additionally, the refractive index of MF signals varies slowly in pure coal, thus the signals travel on a straight line path. Propagation in coal takes the form of a parallel plane, transverse electromagnetic (TEM) transmission-line type mode, with the electric field vertical and the magnetic field horizontal within a planar seam bounded above and below by more conductive rock. Seam anomalies such as rock have a different refractive index than coal, thereby deflecting the signal path to a greater degree. The narrowband-FM signals allow for measurement of this path attenuation thus providing a second means of detecting anomalies. Finally, phase shift of the FM signal along the path also indicates the presence of anomalous formations within the seam.

When greater resolution is desired tomographic, rather than continuity imaging techniques are employed. Tomography results in high resolution by employing the lowest attenuation-rate frequency and making more frequent spatial measurements. The attenuation rates are measured at each spatial orientation of transmitter and receiver and the resulting data points are analyzed using computer aided imaging techniques to yield a pictorial representation of the anomaly.

To obtain good resolution, the distance between the transmitter and receiver should be greater than [$\lambda_c/2$] $\lambda_c/2\pi$ where $\lambda_c$ is the signal wavelength in coal. Thus for the 520 kHz transmission frequency of the preferred embodiment, the wavelength in coal is 97.7 meters. This yields a minimum separation distance of 15.56 meters.

The in-seam tomographic imaging method as illustrated in FIG. 5, accordingly is carried out with portable entry receiver 10 and transmitter 20 in a manner determined to maximize resolution. Tuned loop antenna 21 of transmitter 20 is designed to excite the natural coal seam mode azimuthal magnetic field components ($H_\phi$), at a preselected wavelength in the 400–800 kHz range, thus providing the highest field strength at a given power output. Receiver tuned loop antenna 11 is placed in a co-planar alignment with transmitter antenna 21 to ensure maximum field strength. The instruments are separated by a distance of more than 15.6 meters for maximum resolution. In the preferred embodiment, a coal seam is 600 feet (200 meters) wide, thus ensuring adequate separation. It can be seen that a coal seam 70 contains within it a rock/sand barrier 74. This rock/-sand barrier 74 will act as a radiogenic mass and cause an attenuation in the transmitted signal. Because tomography employs the lowest attenuation-rate signal frequency allowing for minimization of transmitter output power, it is important that the head and tail-gate entries do not include continuous electrical conductors. Such conductors create secondary magnetic fields that would interfere with received signal level measurements. To obtain adequate resolution in the tomographic in-seam survey a number of data must be collected by taking frequency spatial measurements. The procedure is thus carried out by making a series of received signal level measurements at specific locations (designated as $X_0$, $X_1 \ldots X_n$) in the tail gate entry 76 for each transmitter location in the head gate entry 78. Similarly the transmitter 20 is placed at a series of specific locations (designated as $Y_0$, $Y_1 \ldots Y_n$) within the head-gate entry 78 and the receiver 10 is placed at the corresponding locations in the tail-gate entry 76. At each receiver location in the entry way distance logging keyboard 12 is used to enter coordinates representing the receiver's position relative to the transmitter. These coordinates are converted to digital signals and stored, along with the measured received signal values, on the magnetic tape. In reconstructing the data, the signal strength measurements can be thus corrected for positional changes of the transmitter and receiver. The longitudinal spacing of transmitter and receiver locations is determined by the required image resolution. The resultant received signal data is converted to digital form and stored on the cassette tape 13 of receiver 10 and can be analyzed in a computer based tomography algorithm. Such computer aided imaging algorithms will provide a detailed picture of the seam structure. Computer generated data may also include a print-out of seam parameters (conductivity, ash content, etc.) and a digital tape for use by the mines' computer graphics terminal.

Surface based seam imaging equipment is deployed as shown in FIG. 6. The coal seam to be imaged is represented by general reference character 80. It can be seen that a fault 82 is present within the seam. In employing the surface base imaging procedure using a perimeter exploration protocol a plurality of drill holes 84 are drilled along the perimeter of the longwall panels. In the preferred embodiment two adjacent longwall panels, of a combined width of 1200 feet and a length of 6000 feet can be imaged with a ten-hole drilling plan. Such a drilling plan will detect seam anomalies within the panels. If a fault is detected in the panel a convergent search strategy is required to determine its heading. Such a search strategy is carried out by drilling bisecting boreholes within the perimeter to localize the fault. Surface imaging of the coal seam is accomplished in a manner similar to the in-seam imaging procedure. After the series of drill holes have been bored around the perimeter of the longwall panel, the surface probes 30 are inserted down the boreholes 84 to the depth of the coal seam which has been determined from the core samples. FIG. 6 illustrates a vertical displacement fault which results in one end of the coal seam being deeper then the other. Because the signals tend to propagate through the coal. The receiver probe 30 is placed within the coal seam and not necessarily at the same depth as the transmitter probe 30. Downhole probes 30, comprising a receiver probe and a transmitter probe are inserted in opposite drill holes 84. Receiver and transmitter antenna segments 48 are aligned in a co-planar manner by means of drive motors 49 located in the end of downhole probes 30. Antenna headings are determined and controlled through the use of surface control units 85 including telemetry and control equipment and a modem. These units, together with the probe control equipment and cabling, are mounted in trucks 86. Continuous wave FM medium frequency (CWMF) transmissions are made in a manner similar to those made in the in-seam imaging procedure and attenuation rate and/or phase shift are measured. The process is repeated with the receiver probe 30 and transmitter probe 30 in each of the boreholes 84.

This surface procedure may also be carried out from an underground surface. This situation occurs when a lower coal seam is being explored from an existing mined seam. The existing seam floor then becomes the surface into which boreholes are drilled for exploration of the lower seam. The downhole probes 30 are inserted into the boreholes and measurements taken in the normal surface exploration manner.

The resultant continuity data are analyzed to determine if areas of increased attenuation are present. Such areas indicate fault zones or other geological anomalies. If sufficient boreholes are drilled, the data can be analyzed using computer-aided tomographic imaging techniques to yield a pictorial result as with the in-seam procedure.

Additionally, floor/roof rock characteristics can be determined using continuous wave medium frequency continuity measurements. This procedure is analogous to the downhole seam continuity measurements except the receiver and transmitter probes 30 are positioned above the coal seam ceiling to measure roof conditions, and just below the floor to measure floor conditions. The signals are thus propagated through the surrounding rock, and signal attenuation is measured. In this way a determination respecting the type of rock and resulting roof/floor conditions can be made.

Figure 7:
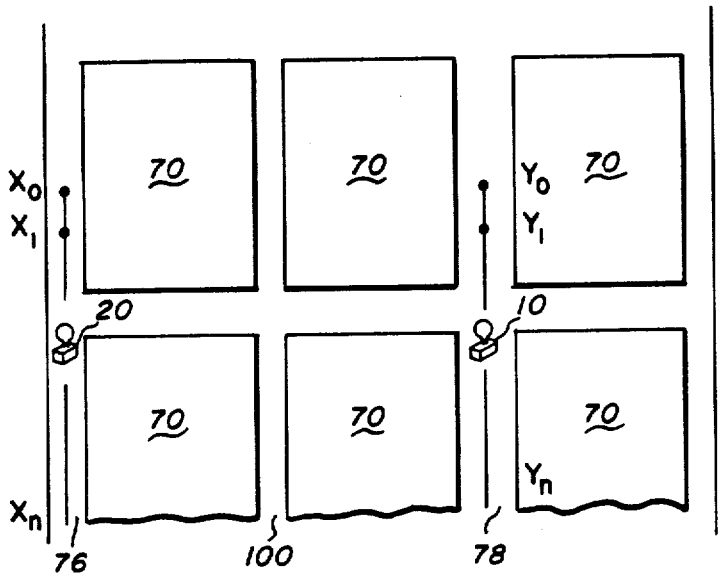
FIG. 7 is an idealized top plan view of a coal seam showing a roof rock imaging method.

Roof rock characteristics can also be determined by placing the in-seam receiver 10 and transmitter 20 within the tail gate and head gate entries 76 and 78 at very close intervals, for example, on the order of twenty five feet, and analyzing the resulting data using a backplane and/or reconstruction algorithm to develop an isopach map of constant attenuation rates. FIG. 7 illustrates a method for imaging roof rock conditions in a developing entry 100, which is mined between the existing entries 76 and 78. The receiver 10 is placed at a series of locations ($X_0$, $X_1$ . . . $X_n$), for example, within the entry 76 and the transmitter 20 is placed at a series of locations ($Y_0$, $Y_1$ . . . $Y_n$) for example, within the entry 78, with the developing entry 100 between the entries 76 and 78. Attenuation rates are determined by propagating the medium frequency signals from the transmitter 20 to the receiver 10, and a backplane and/or reconstruction algorithm may be used to analyze the resulting data. For improved imaging, the intervals between instrument locations may be short, for example, twenty-five feet or less. It may be noted that this method can be used to image a single developing entry 100, or multiple entries 100 between existing entries 76 and 78.

Figure 8:
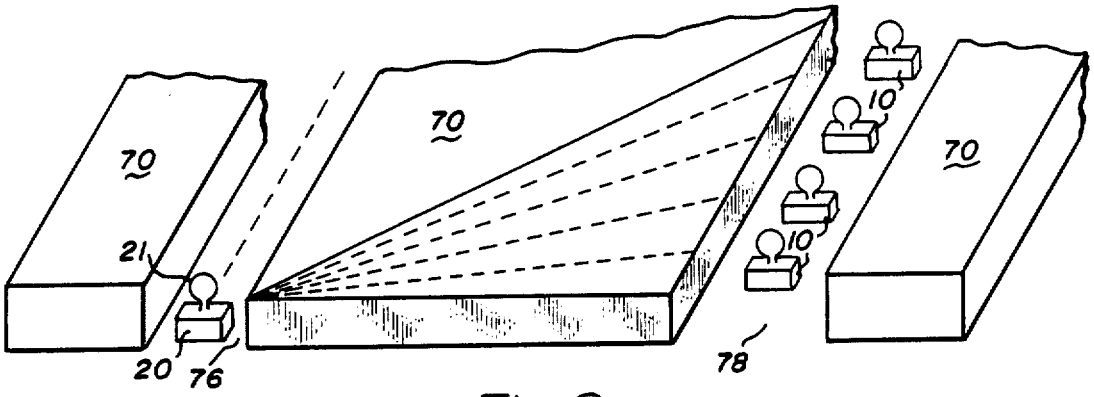
FIG. 8 is an idealized cut-away view of a coal seam showing a multiple instrument survey method.

FIG. 8 illustrates a survey procedure using a single transmitter 20 and multiple receivers 10 placed within the coal seam 70. This procedure speeds up acquisition of the necessary data, and works equally well with a single receiver 10 and multiple transmitters 20 or multiple receivers 10 and transmitters 20.

Figure 9:
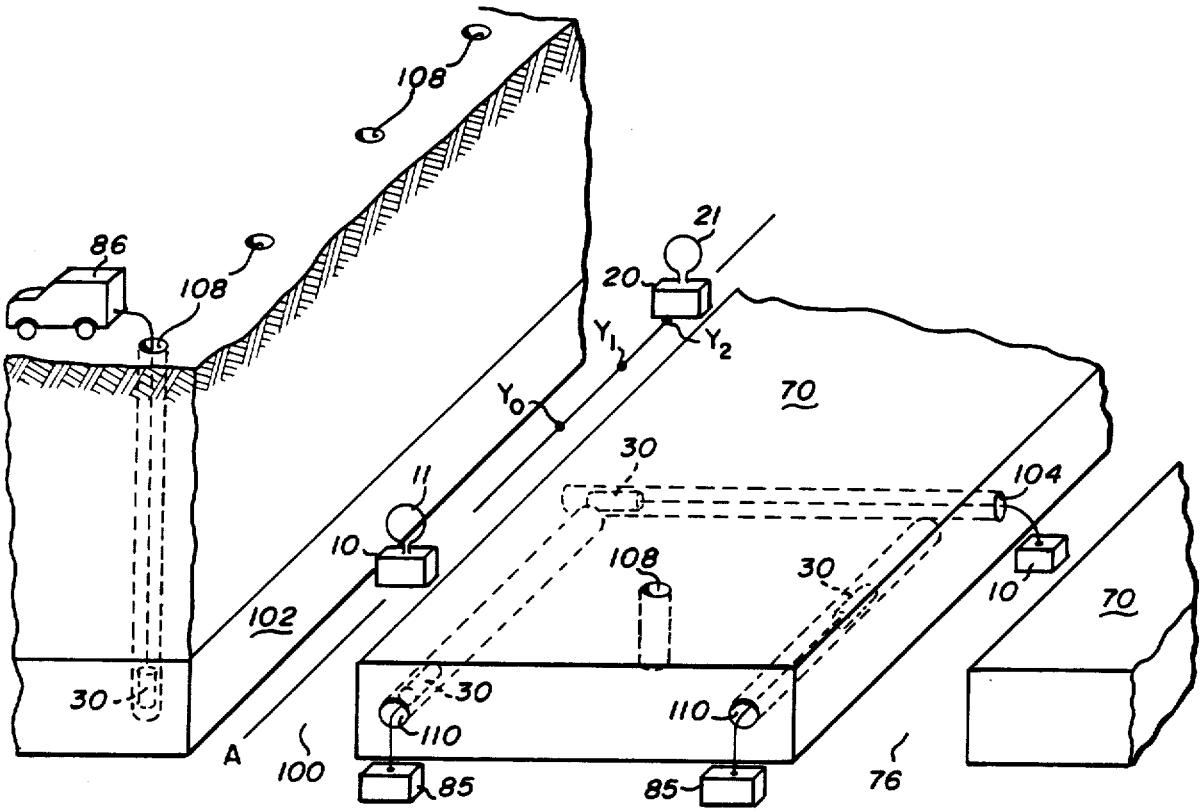
FIG. 9 is an idealized cut-away view of a coal seam showing survey procedures utilizing combinations of in-seam and downhole equipment with vertical boreholes and horizontal drillholes.

Numerous variations on the in-seam and downhole survey techniques can be utilized for specific purposes. As illustrated in FIG. 9, the downhole probes 30 may be used in conjunction with an in-seam receiver 10 and/or transmitter 20 in a crosshole survey method to obtain high resolution imaging of anomalies that may exist in a virgin local seam 102 next to the developing entry 100. Backplane reconstruction and/or tomography algorithms may be used to analyze the resulting data.

FIG. 9 also illustrates a method for measuring seam heights along a horizontal in-seam drillhole 104. This method makes use of the crosshole method using an in-seam transmitter 20, and a downhole-type probe 30 which is inserted into the horizontal drillhole 104, which is drilled perpendicular to a transmitter survey line A. The receiver 30 is laterally displaced within the drillhole 104 and signal attenuation readings are taken at various points for each of a plurality of transmitter locations designated as $Y_0$, $Y_1$, . . . $Y_n$. A plot of attenuation rate versus displacement of the instrument in the horizontal borehole 104 can be analyzed to determine seam heights along the drillhole 104. While this method is intended for use with coal seams 70 which have preexisting entries 76 and 78 or developing entries 100 for positioning an in-seam instrument 10 or 20, the method can also be used with a downhole probe 30 inserted into a plurality of boreholes 108 which are in a line perpendicular to the drillhole 104. Also illustrated in FIG. 9 is a method of guided parallel in-seam drilling to image the seam 70 between a pair of horizontal longitudinal drillholes 110. The downhole-type instruments 30 are inserted into the drillholes 110 and multiple readings are made at various transmitter and receiver locations as with all of the survey procedures. A variation on this procedure is to drill both the longitudinal horizontal drillhole 110 and the transverse drillhole 104, with radio wave transmission occurring diagonally between the drillholes 104 and 110. As with all of these methods, a vertical downhole instrument may be used in conjunction with one or both of the horizontally displaceable instruments. It may be noted that with modern directional drilling technology, horizontal in-seam drillholes can be drilled from surface drill rigs, thus further expanding the scope of the drillhole survey procedure. The drillholes 110 and/or 104 may be drilled, for example, at different heights within the seam 70. Any of the foregoing in-seam survey procedures may also be used to image cavings in block caving mining.

Figure 10:
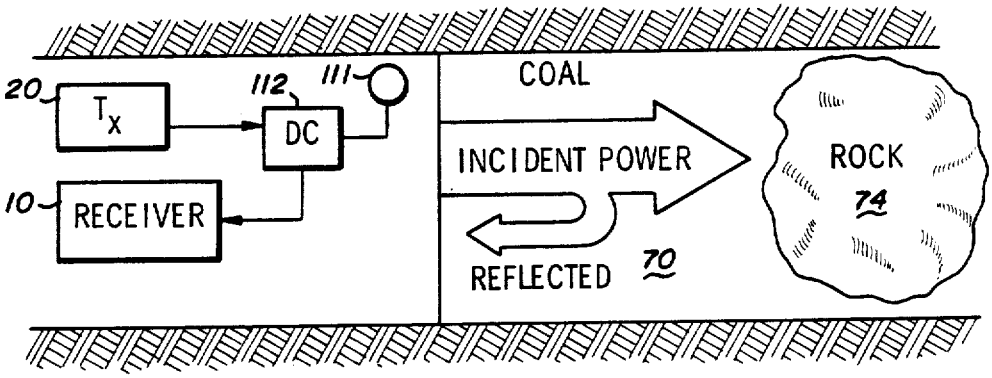
FIG. 10 is an idealized top plan view of instruments and a procedure for verification of an in seam anomaly.

Anomalies detected by any of the foregoing survey methods can be verified by a comparison of direct and reflected signals. A transmitter, which may be the in-seam instrument 20 or the downhole instrument 30, is positioned in the seam 70, as illustrated in FIG. 10, to propagate continuous wave MF signals towards the anomaly 74. A receiver, either the in-seam instrument 10 or the downhole probe 30 is positioned adjacent to the transmitter to receive a reflected signal from the anomaly 74. A signal from a transmitter/receiver loop antenna 111 is propagated by a first port of a directional coupler 112 and then to the anomaly 74, which reflects part of the signal. The reflected signal enters a second port of the coupler 112 via the antenna 111, and within the coupler 112 a comparison of direct and reflected signal power is made. The presence of the anomaly 74 will cause an increase in reflected power over that reflected by the seam 70.

Once an anomaly has been imaged in a coal panel 70, its effect on longwall mining can be ameliorated by separating the longwall into pieces, for example a first piece which would avoid the anomaly and a second piece which would run into it. A take-down room and a set-up room are mined, using continuous mining techniques, on either side of the anomaly and perpendicular to the longwall heading. The entire longwall is operated until the second part enters the take-down room, at which point this part is taken down and reset in the set-up room. The first part of the longwall meanwhile continues to operate and is relinked with the second part on the far side of the anomaly. An alternative to allow uninterrupted longwall mining of the panel is to fracture the anomaly by any means known in the art, for example, by fracking with high pressure injections of mud, or high expansion rosins, or by conventional blasting.

Figure 11:
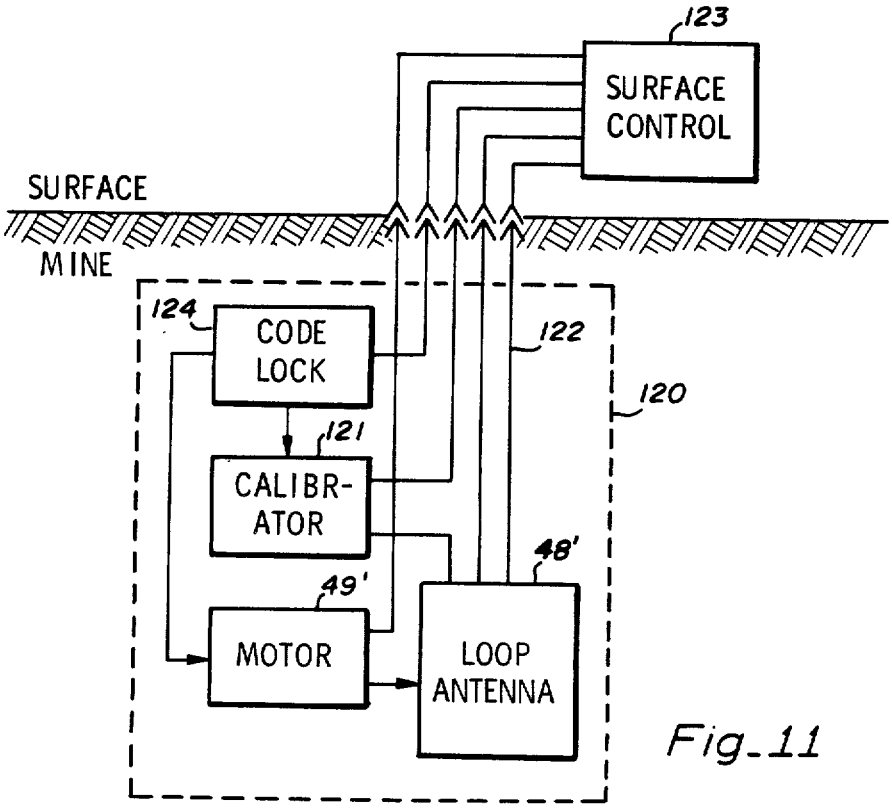
FIG. 11 is a schematic view of an alternative embodiment of a downhole probe of the present invention.

Boreholes on the order of 1700 feet or more are costly and time consuming to drill and expensive to case. The lack of casing causes the hole to close after the drill stem is removed. For such boreholes, an alternative embodiment of the probe 30, illustrated in schematic in FIG. 11, may be utilized. These probes, designated by the reference character 120 essentially comprise a loop antenna 48', a motor 49' mechanically coupled to the antenna 42' for rotating the antenna 42' about a vertical axis, a voltage level calibrator circuit 121 and a cable 122 for coupling to a power and control means 123. The surface power and control unit 123 includes transmitter and/or receiver circuitry for delivering signals to or receiving signals from the loop antenna 48'. Both electrical power and intelligence signals are carried from the unit 123 to the probe 120, and intelligence signals are carried back to the unit 123, via the cable 122. The voltage level calibrator circuit 121 generates a precision signal level for calibrating the entire signal path from the antenna to the control means 123. The probe 120 can be left in the borehole for extended time periods while a drilling protocol is completed, and may be used at any time as desired. The probe 120 may also include a security code lock circuit 124 in order to prevent unauthorized use of the probe 100. Typically, the probes 120 will be inserted into the borehole through PVC piping, or they may be inserted directly through the drill stem. The pipe or stem is subsequently removed, leaving the probe 120 in place in the borehole.

Although the present invention has been described in terms of the presently preferred embodiments, it is to be understood that such disclosure is not to be interpreted as limiting. Various alterations and modifications will no doubt become apparent to those skilled in the art after having read the disclosure. Accordingly, it is intended that the appended claims be interpreted as covering all alterations and modifications as fall within the true spirit and scope of the invention.

In the claims:

1. A method for detecting geological anomalies in underground coal seam formations comprising placing an FM transmitter having continuous wave transmit capabilities in a medium frequency range of between approximately 300 KHz to approximately 800 KHz about a coal seam to be analyzed, the transmitter including a tuned-loop antenna for propagation through said seam;

placing a medium frequency FM receiver having continuous wave receive capability and including a tuned-loop antenna about said seam remote from the position of the transmitter with said seam intermediate to the transmitter and receiver, said tuned-loop antennas of the receiver and transmitter being positioned to be vertical to said seam, said receiver further including measuring and recording means for measuring and recording a plurality of characteristics of said received waves propagated through said seam;

exposing said seam to a plurality of transmissions of continuous wave medium frequency waves with an azimuthal magnetic field component propagated horizontally through said seam from the transmitter towards the receiver;

measuring a plurality of signal transmission characteristics through said seam;

generating a number of data points by locating both the transmitter and receiver at several points about said seam such that for each transmitter location the receiver is placed at a plurality of preselected points about said seam;

calculating a plurality of expected signal transmission characteristics through said seam; and comparing said calculated signal transmission characteristics with said measured signal transmission characteristics and generating a graphical representation of said formation thereform.

2. The method of claim 1 wherein the resulting data are analyzed with a computer based tomography algorithm wherein a graphical representation of the coal seam anomaly is produced.

3. The method of claim 1 further comprising drilling a plurality of first set of boreholes adjacent to one side of said coal seam to be imaged and drilling a plurality of a second set of boreholes opposite to the seam, with the seam intermediate to the first and second sets of boreholes;

sequentially inserting into each of the first set of boreholes said medium frequency transmitting probe and inserting into a plurality of the second set of boreholes said medium frequency receiving probe, the receiving and transmitting probes being inserted into said boreholes to the depth of said coal seam and approximately equal in depth to each other;

transmitting medium frequency signals from said transmitter probe in each of the first set of boreholes to said receiver probe in said plurality of the second set of boreholes such that for each transmitter location signals are sent to a receiver probe at each of a plurality of said second set of boreholes, and measuring a plurality of signal characteristics at each location;

calculating a plurality of expected signal transmission characteristics through said coal seam;

detecting seam anomalies by comparing said measured characteristics along each transmission pathway with said calculated signal characteristics determined by the coal seam composition, and by comparing path attenuation along the different paths; and analyzing the data with computer aided imaging techniques to provide representations of the resultant anomalies.

4. The method of claim 3 wherein the boreholes are drilled approximately 1200 feet apart.

5. The method of claim 3 wherein seam anomalies are localized by drilling additional bisector drillholes between the original drillholes where high signal attenuation occurs, and by generating additional data points therefrom.

6. The method of claim 1 wherein the underground formation is a coal formation; and the anomaly is a coal seam fire.

7. The method of claim 1 wherein said signal transmission characteristics include signal field strength.

8. The method of claim 1 wherein said transmitter further includes an output-connector means for transmitting a reference signal therethrough;

said receiver further includes an input-connector means for receiving said reference signal;

said reference signal input and output-connector means are coupled to a reference signal transmission means; and said measured signal transmission characteristics include a phase shift determined by transmitting said reference signal through said reference signal transmission means and comparing said transmitted reference signal with said signals transmitted through said coal seam.

9. The method of claim 1 wherein said measured signal transmission characteristics include signal field strength; and said calculated signal transmission characteristics include signal field strength.

10. The method of claim 1 wherein said medium frequency range is between approximately 400 KHz and 800 KHz.

11. The method of claim 1 wherein said tuned loop antennas are positioned to be coplanar.

12. The method of claim 1 wherein, at least one receiver is positioned in a downhole location if a transmitter is positioned in an in-seam location, and at least one transmitter is positioned in a downhole location is a receiver is positioned in an in-seam location.

13. The method of claim 1 wherein, a plurality of transmitters and receivers are placed about the seam, and a plurality of data points may be generated simultaneously.

14. The method of claim 1 wherein, a horizontal drillhole is drilled transversely into the seam, and a downhole instrument is inserted at various points therein.

15. The method of claim 1 wherein, the geological anomaly is a roof rock condition; and the transmitter is placed at a plurality of locations about a first lateral edge of the seam, the receiver is placed at a plurality of locations about a second lateral edge of the seam opposite to said first edge, and the coal seam and a developing entry are intermediate to the transmitter and receiver locations.

16. The method of claim 1 wherein, at least a first and a second horizontal drillhole are drilled into the seam, the transmitter being inserted into said first drillhole and the receiver being inserted into said second drillhole, and said continuous wave FM signals being transmitted therebetween for various transmitter and receiver locations within said drillholes.

17. The method of claim 16 wherein, said first and said second drillholes are parallel to each other and longitudinal along the seam.

18. The method of claim 16 wherein, said first and second drillholes are perpendicular to each other.

19. The method of claim 16 and further including, at least one vertical borehole and downhole probe associated therewith, with transmission of continuous wave FM signals occurring between the vertical borehole and at least one of the horizontal drillholes.

20. The method of claim 1 wherein, the seam anomalies are verified by, (a) placing the transmitter with the seam proximate to the anomaly and placing the receiver adjacent to the transmitter;

(b) coupling the transmitter to a directional coupler and sending a direct signal therethrough towards the anomaly within the seam, and receiving in the directional coupler a reflected signal; and (c) comparing a relative signal strength of reflected and direct signals in the directional coupler whereby a low ratio of reflected to direct signal strength indicates the absence of an anomaly and a high ratio indicates the presence of the anomaly.

* * * * *